(12) United States Patent
Mitsui et al.

(10) Patent No.: US 10,527,696 B2
(45) Date of Patent: Jan. 7, 2020

(54) MAGNETIC RESONANCE IMAGING APPARATUS AND SAR COMPUTING METHOD (71) Applicant: TOSHIBA MEDICAL SYSTEMS CORPORATION, Otawara-Shi (JP)

(72) Inventors: Shinji Mitsui, Nasushiobara (JP); Sadanori Tomiha, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 811 days.

(21) Appl. No.: 14/701,624

(22) Filed: May 1, 2015

(65) Prior Publication Data

US 2015/0323629 A1    Nov. 12, 2015

(30) Foreign Application Priority Data

May 7, 2014 (JP) .................................. 2014-096201

(51) Int. Cl.
*G01R 33/54* (2006.01)
*A61B 5/055* (2006.01)

(52) U.S. Cl.
CPC .......... *G01R 33/546* (2013.01); *G01R 33/54* (2013.01); *A61B 5/055* (2013.01)

(58) Field of Classification Search
CPC ... G01R 33/228; G01R 33/58; G01R 33/4828
See application file for complete search history.

(56) References Cited

U.S. PATENT DOCUMENTS

| 7,355,404 B1* | 4/2008 | Hariharan | G01R 33/543 324/307 |
| 2006/0047198 A1* | 3/2006 | Sugimoto | A61B 5/055 600/410 |
| 2007/0247155 A1* | 10/2007 | Zhu | G01R 33/288 324/318 |
| 2009/0093704 A1* | 4/2009 | Ma | A61B 5/417 600/410 |
| 2011/0148411 A1* | 6/2011 | Bottomley | G01R 33/288 324/309 |
| 2012/0262174 A1* | 10/2012 | Voigt | G01R 33/246 324/309 |

(Continued)

FOREIGN PATENT DOCUMENTS

| JP | 08-038447 | 2/1996 |
| JP | 2008-295925 | 12/2008 |

(Continued)

*Primary Examiner* — Huy Q Phan
*Assistant Examiner* — Dustin R Dickinson
(74) *Attorney, Agent, or Firm* — Oblon, McClelland, Maier & Neustadt, L.L.P.

(57) ABSTRACT

A magnetic resonance imaging apparatus includes a static magnetic field generator, a gradient magnetic field generator, a transmission coil and a processing circuitry. The static magnetic field generator generates a static magnetic field. The gradient magnetic field generator generates a gradient magnetic field. The transmission coil applies an RF pulse to an object. The processing circuitry determines high frequency pulse power absorbed by other than the object in accordance with a volume of the object and computes a specific absorption rate (SAR) with the determined high frequency pulse power.

11 Claims, 5 Drawing Sheets

(56) References Cited

U.S. PATENT DOCUMENTS

| | | | | |
|---|---|---|---|---|
| 2014/0249612 A1* | 9/2014 | Bonmassar | ........ | C09K 19/3809 |
| | | | | 607/116 |
| 2015/0268321 A1* | 9/2015 | Zhai | .................... | G01R 33/288 |
| | | | | 324/309 |

FOREIGN PATENT DOCUMENTS

| | | |
|---|---|---|
| JP | 2013-31633 | 2/2013 |
| JP | 2014-61279 | 4/2014 |
| WO | WO 2014/064553 A1 | 5/2014 |

* cited by examiner

|  |  | IMAGING REGION | | | |
|---|---|---|---|---|---|
|  |  | ABDOMEN | HEAD | ANKLE | ... |
| WEIGHT CLASS | w1 | F1 | F2 | F3 |  |
|  | w2 | F4 | F5 | F6 |  |
|  | w3 | F7 | F8 | F9 |  |
|  | w4 | F10 | F11 | F12 |  |
|  | ⋮ |  |  |  |  |

MAGNETIC RESONANCE IMAGING APPARATUS AND SAR COMPUTING METHOD

CROSS-REFERENCE TO RELATED APPLICATION

This application is based upon and claims the benefit of priority from Japanese Patent Application No. 2014-96201, filed on May 7, 2014, the entire contents of which are incorporated herein by reference.

FIELD

An embodiment as one aspect of the present invention relates to a magnetic resonance imaging (MRI) apparatus and a specific absorption rate (SAR) computing method.

BACKGROUND

MRI is an imaging technique in which a radio frequency (RF) pulse of Larmor frequency is emitted to cause magnetic excitation of a nucleus spin of an object placed in a static magnetic field, and nuclear magnetic resonance (NMR) signals are generated by this excitation to be used for reconstructing of images. In MRI, an RF coil is used to transmit an RF pulse to an imaging region to elicit nuclear magnetic resonance.

In this frequency range, the RF pulse causes an increase in body temperature of the object. Accordingly, from the viewpoint of safety, output power (RF pulse power) of the RF pulse to be transmitted to the object has an upper limit (limit value) specified by, for example, the International Electrotechnical Commission (IEC) standard or other standards. It is necessary to compute an absorption amount of RF pulse per unit time and per unit mass as a specific absorption rate (SAR), and to manage transmission so that SAR does not exceed the limit value. The SARs to be managed include a whole body SAR, a body part SAR, a head SAR, and a local SAR.

Specifically, output power (RF power) of an RF pulse signal supplied to the transmission coil is acquired, and the acquired RF power is used for SAR computing. A conventional whole body SAR ($SAR_W$) is computed by Expression (1) based on an RF power $P_W$ in a loaded condition, which are predicted based on an RF power obtained in prior imaging and imaging conditions, an RF power $P_e$ in an unloaded condition, and an entire weight $W_W$ of the object. A conventional body part SAR ($SAR_I$) is computed by Expression (2) based on a body part PI of the RF power $P_W$ in the loaded condition, the RF power $P_e$ in the unloaded condition, and a partial weight $W_I$. A conventional head SAR ($SAR_H$) is computed by Expression (3) based on a head portion $P_H$ of the RF power $P_W$ in the loaded condition, the RF power $P_e$ in the unloaded condition, and a head weight $W_H$.

$$SAR_W [W/kg] = \frac{P_W[W] - P_e[W]}{W_W[kg]} \quad (1)$$

$$SAR_I [W/kg] = \frac{P_I[W] - P_e[W]}{W_I[kg]} \quad (2)$$

$$SAR_H [W/kg] = \frac{P_H[W] - P_e[W]}{W_H[kg]} \quad (3)$$

When the whole body SAR, the body part SAR, and the head SAR are computed based on Expressions (1) to (3), the RF power $P_e$ in the unloaded condition is used in each of the cases. As the RF power $P_e$ in the unloaded condition, a fixed value obtained by measuring a pseudo human body model (phantom), which does not become a load as viewed from the transmission coil, is used.

A technology relating to an MRI apparatus which reduces artifacts and SARs is disclosed as a conventional technology relating to the present invention.

Although the RF power in the unloaded condition should be defined as an RF power absorbed by other than the object, a fixed value is used in the conventional technology. Accordingly, the fixed value may be inappropriate depending on a volume or a body fat percentage of the object (imaging region) due to an interaction between the transmission coil and the object, such as coupling therebetween. If the RF power in the unloaded condition is not appropriate, the SAR becomes too large and imaging is excessively limited, which results in a defect of deteriorated convenience, or the SAR becomes too small and imaging is permitted beyond limits, which results in a defect of deteriorated safety.

BRIEF DESCRIPTION OF THE DRAWINGS

In accompanying drawings.

DETAILED DESCRIPTION

An MRI apparatus and an SAR computing method according to an embodiment is described with reference to accompanying drawings.

To solve the above-described problems, the present embodiment provides the MRI apparatus, including: a static magnetic field generator configured to generate a static magnetic field; a gradient magnetic field generator configured to generate a gradient magnetic field; a transmission coil configured to apply an RF pulse to an object; and a processing circuitry configured to determine high frequency pulse power absorbed by other than the object in accordance with a volume of the object and to compute a specific absorption rate (SAR) with the determined high frequency pulse power.

To solve the above-described problems, the present embodiment provides the MRI apparatus, including: a static magnetic field generator configured to generate a static magnetic field; a gradient magnetic field generator configured to generate a gradient magnetic field; a transmission coil configured to apply an RF pulse to an object; a processing circuitry configured to determine a coefficient in accordance with a volume of the object, the coefficient being multiplied by high frequency pulse power supplied to the transmission coil in an unloaded condition, and to compute an SAR by using not the high frequency pulse power in an unloaded condition but by a value obtained by multiplying the high frequency pulse power in the unloaded condition by the coefficient.

To solve the above-described problems, the present embodiment provides the SAR computing method in a magnetic resonance imaging apparatus including a static magnetic field generator, a gradient magnetic field generator and a transmission coil configured to apply an RF pulse to an object, the method comprising determining high frequency pulse power absorbed by other than the object in accordance with a volume of the object and to compute an SAR with the determined high frequency pulse power.

Figure 1:
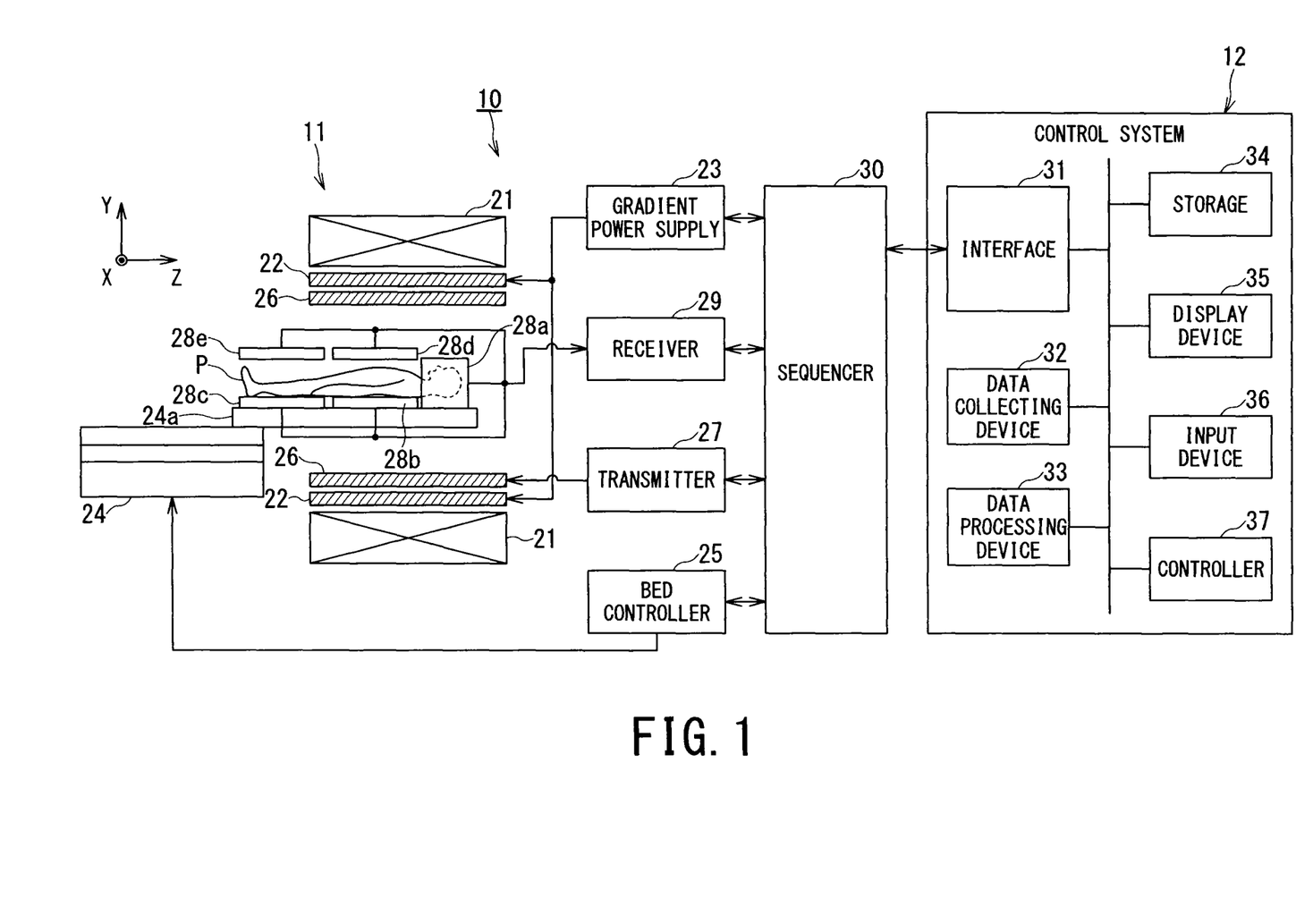
FIG. 1 is a schematic view illustrating a hardware configuration of an MRI apparatus according to a present embodiment.

FIG. 1 is a schematic view illustrating a hardware configuration of an MRI apparatus according to a present embodiment.

FIG. 1 illustrates an MRI apparatus 10 according to the present embodiment configured to image an imaging region of an object (patient) P. The MRI apparatus 10 is mainly made up of an imaging system 11 and a control system 12.

The imaging system 11 includes a static magnetic field magnet 21, a gradient magnetic field coil 22, a gradient power supply 23, a bed 24, a bed controller 25, a transmission coil (RF coil for transmission) 26, a transmitter 27, reception coils (RF coils for reception) 28a to 28e, a receiver 29, and a sequencer (sequence controller) 30.

The static magnetic field magnet 21 is a static magnetic field generator formed into a hollow cylindrical shape in an outermost portion of a mount (not illustrated). The static magnetic field magnet 21 generates a uniform static magnetic field in its internal space. Examples of the static magnetic field magnet 21 include a permanent magnet, a resistive magnet, a superconducting magnet, and the like.

The gradient magnetic field coil 22 is a gradient magnetic field generator formed into a hollow cylindrical shape. The gradient magnetic field coil 22 is arranged inside the static magnetic field magnet 21 to generate a gradient magnetic field in an internal space thereof. The gradient magnetic field coil 22 is formed from a combination of three coils each corresponding to X, Y, and Z axes which are orthogonal to each other. These three coils individually receive current supply from a later-described gradient power supply 23 and generate gradient magnetic fields where the intensities of the magnetic fields vary along each of X, Y, and Z axes. A Z-axis direction is aligned with the static magnetic field.

The gradient magnetic fields generated by the gradient magnetic field coil 22 along each of X, Y, and Z axes correspond to, for example, a gradient magnetic field Gr for readout, a gradient magnetic field Ge for phase encoding, and a gradient magnetic field Gs for slice selection, respectively. The gradient magnetic field Gr for readout is used to change the frequency of a nuclear magnetic resonance (NMR) signal in response to a spatial location. The gradient magnetic field Ge for phase encoding is used to change the phase of an NMR signal in response to the spatial location. The gradient magnetic field Gs for slice selection is used to determine an arbitrary imaging cross section.

The gradient power supply 23 supplies current to the gradient magnetic field coil 22 based on pulse sequence execution data sent from the sequencer 30.

The bed 24 includes a table-top 24a to lay the object P thereon. Under the control of the later-described bed controller 25, the bed 24 inserts the table-top 24a into a hollow (imaging port) of the gradient magnetic field coil 22 with the object P being laid thereon. The bed 24 is generally arranged so that its longitudinal direction is parallel to a central axis of the static magnetic field magnet 21.

Under the control of the sequencer 30, the bed controller 25 drives the bed 24 so as to move the table-top 24a in a longitudinal direction and a vertical direction. The transmission coil 26 is arranged inside the gradient magnetic field coil 22 to generate an RF pulse upon reception of an RF pulse signal supplied from the transmitter 27.

The transmitter 27 transmits an RF pulse signal corresponding to the Larmor frequency to the transmission coil 26 based on pulse sequence execution data sent from the sequencer 30.

Figure 2:
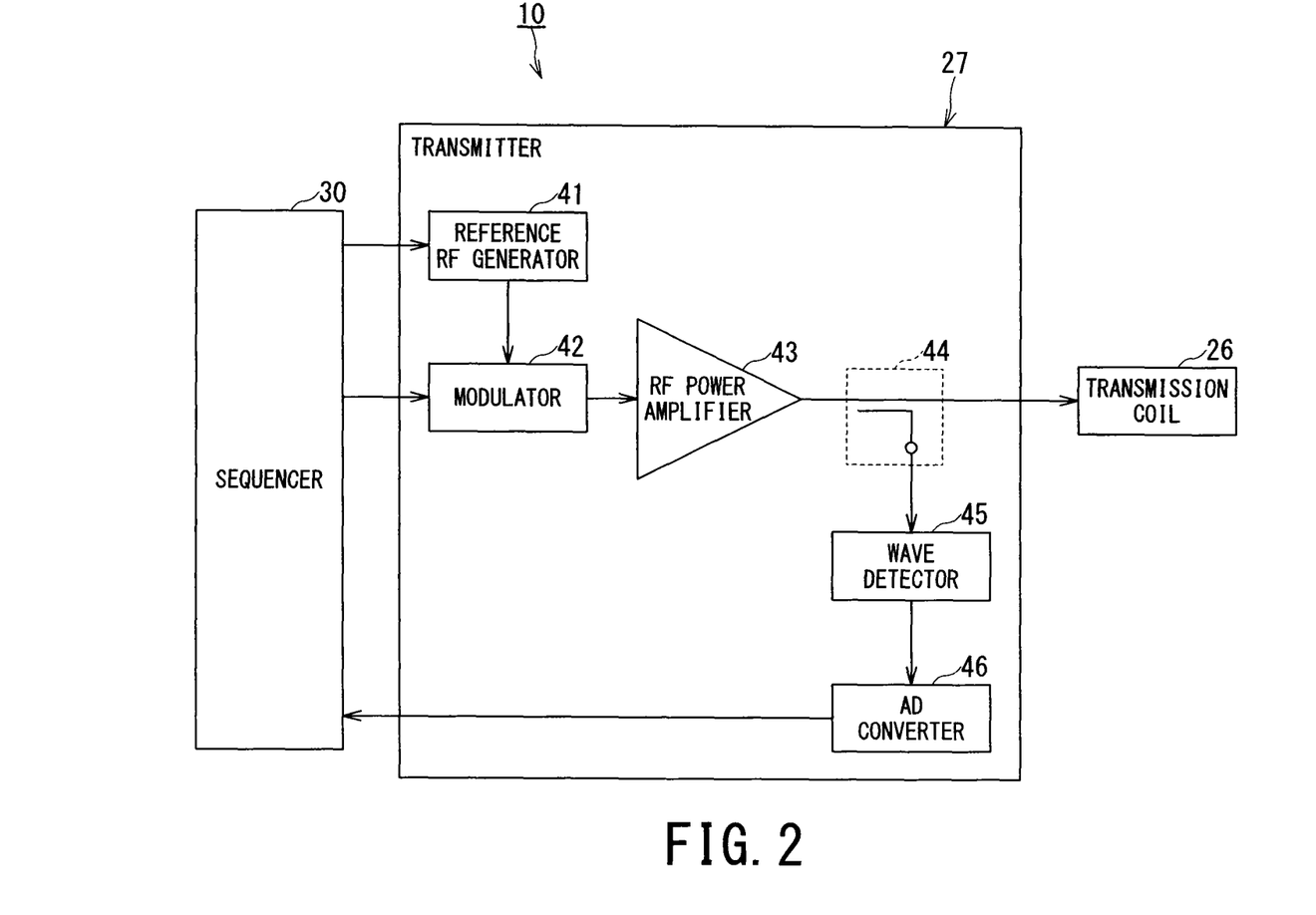
FIG. 2 is a diagram illustrating a configuration example of a transmitter.

FIG. 2 is a diagram illustrating a configuration example of the transmitter 27.

As illustrated in FIG. 2, the transmitter 27 includes a reference RF generator 41, a modulator 42, an RF power amplifier 43, a directional coupler 44, a wave detector 45, and an analog to digital (AD) converter 46.

The reference RF generator 41 generates a reference RF signal (RF carrier wave) under the control of the sequencer 30.

The modulator 42 modulates the reference RF signal generated in the reference RF generator 41 to an RF pulse signal of a specified waveform under the control of the sequencer 30.

The RF power amplifier 43 amplifies the RF pulse signal modulated in the modulator 42 and provides the amplified pulse RF signal to the transmission coil 26 via the directional coupler 44. The amplified RF pulse signal is transferred to the transmission coil 26, and an RF pulse is emitted from the transmission coil 26 to the object P. The transmission coil includes a transmission coil for whole body and a transmission coil 26 for partial region.

The directional coupler 44 is arranged on a transmission line of the RF pulse signal in non-contact with the transmission line. The directional coupler 44 attenuates the RF pulse signal, which is transferred to the transmission coil 26, with a required degree of coupling (coupling coefficient) and sends the amplified RF pulse signal to a wave detector 45. The directional coupler 44 is a radio frequency device for attenuating electric power of an RF pulse signal (a traveling wave and a reflected wave). An output signal of the directional coupler 44 is detected by the wave detector 45 on an MR signal processing substrate and is digital-converted by an AD converter 46. Output data of the AD converter 46 is used as an RF pulse signal for use in computation of the SAR.

With reference again to FIG. 1, the reception coils 28a to 28e are arranged inside the gradient magnetic field coil 22 to receive NMR signals radiated from the imaging region of the object P due to an influence of the RF magnetic field. Here, the reception coils 28a to 28e are each array coils having a plurality of element coils each of which receives NMR signals radiated from the object P. Upon reception of the NMR signals by each of the element coils, the received NMR signals are output to the receiver 29.

The reception coil 28a is a head coil mounted on a head of the object P. The reception coils 28b and 28c are backbone coils each arranged between a back of the subject P and the table-top 24a. The receiver coils 28d and 28e are abdominal coils each mounted on an abdominal side of the object P.

The receiver 29 generates NMR signal data based on the NMR signals output from the reception coils 28a to 28e based on pulse sequence execution data sent from the sequencer 30. Upon generation of the NMR signal data, the receiver 29 transmits the NMR signal data to the control system 12 via the sequencer 30.

The receiver 29 has a plurality of receiving channels configured to receive the NMR signals output from a plurality of the element coils included in the reception coils 28a to 28e. When an element coil to be used for imaging is notified from the control system 12, the receiver 29 allocates a receiving channel to the notified element coil so as to receive an NMR signal output from the notified element coil.

The sequencer 30 is connected to the gradient power supply 23, the bed controller 25, the transmitter 27, the receiver 29, and the control system 12. The sequencer 30 stores sequence information including control information which is necessary for driving the gradient power supply 23, the bed controller 25, the transmitter 27, and the receiver 29. The control information is, for example, motion control information such as intensity, application time, and application timing of a pulse current and the like that should be applied to the gradient power supply 23.

The sequencer 30 also drives the bed controller 25 in accordance with the stored specified sequence so as to move the table-top 24a back and forth with respect to the mount in Z direction. The sequencer 30 further drives the gradient power supply 23, the transmitter 27, and the receiver 29 in accordance with the stored specified sequence so as to generate an X-axis gradient magnetic field Gx, a Y-axis gradient magnetic field Gy, a Z-axis gradient magnetic field Gz, and an RF pulse signal inside the mount.

The control system 12 performs control of the entire MRI apparatus 10, data collection, image reconstruction, and the like. The control system 12 has an interface 31, a data collecting device 32, a data processing device 33, a storage 34, a display device 35, an input device 36, and a controller 37.

The interface 31 is connected to the gradient power supply 23, the bed controller 25, the transmitter 27, and the receiver 29 via the sequencer 30. The interface 31 controls input/output of the signals delivered and received between each of these connected units and the control system 12.

The data collecting device 32 collects the NMR signal data transmitted from the receiver 29 via the interface 31. The data collecting device 32 collects the NMR signal data and stores the collected NMR signal data in the storage 34.

The data processing device 33 performs post-processing, i.e., reconstruction processing such as Fourier transform, on the NMR signal data stored in the storage 34 so as to generate spectrum data or image data of a desired nucleus spin inside the imaging region of the object P. In the case of imaging a positioning image, the data processing device 33 generates, based on the NMR signals received in each of the plurality of element coils included in the reception coils 28a to 28e, profile data indicating NMR signal distribution in an array direction of the element coils for each of the element coils. The data processing device 33 then stores the generated various data in the storage 34.

The storage 34 stores data, such as NMR signal data collected in the data collecting device 32 and the image data generated in the data processing device 33, for each object P.

The storage 34 stores RF power in the unloaded condition obtained from the AD converter 46 (illustrated in FIG. 2) when the MRI apparatus 10 is installed, and a later-described correspondence table illustrated in FIG. 4.

The display device 35 displays various kinds of information such as image data generated by the data processing device 33, an imaging condition edit screen, and the like. As the display device 35, display devices such as liquid crystal displays may be used.

The input device 36 receives various operations and information inputs from an operator. As the input device 36, input devices such as keyboards may appropriately be used.

The controller 37 is configured by a processor and a memory such as a random access memory (RAM). The controller 37 controls each of the units described before for comprehensive control of the MRI apparatus 10.

The processor means a processing circuitry such as an integrated circuitry for specific uses (ASIC: application specific integrated circuit) and a programmable logic device other than an exclusive or a general-purpose central processing unit (CPU) or a micro-processor unit (MPU). The programmable logic device includes the processing circuitry such as a simple programmable logic device (SPLD), a complex programmable logic device (CPLD) and a field programmable gate array (FPGA). The processor retrieves and executes a program stored in the memory or programmed into oneself, and thereby performs functions illustrated in FIG. 3.

The processor may be configured by a single processing circuitry or may be configured by a combination of a plurality of independent processing circuitries. In the latter situation, the memory storing the program may be established individually every processing circuitry or the storage 34 may store programs corresponding to respective functions of the processing circuitries.

Figure 3:
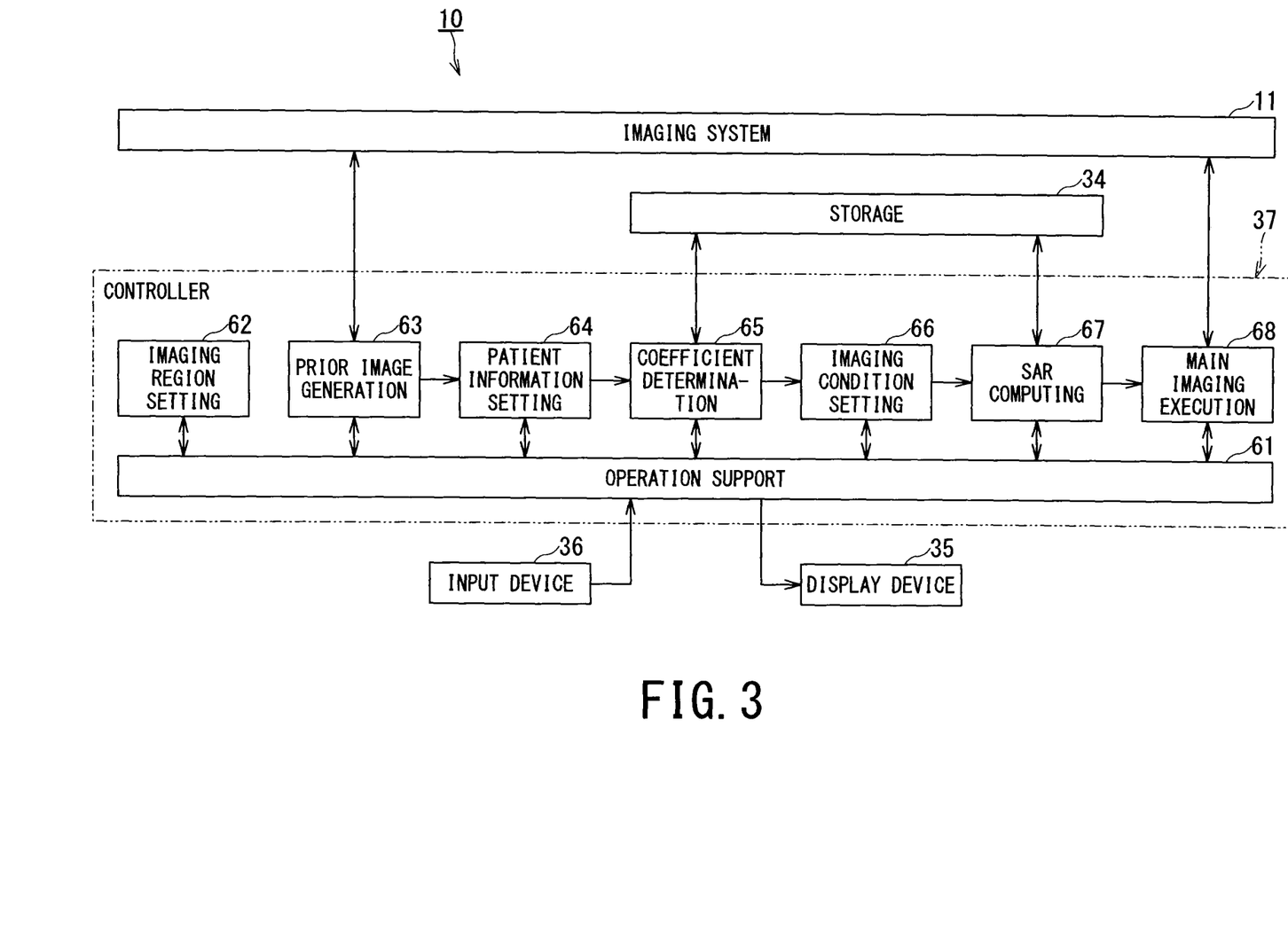
FIG. 3 is a block diagram illustrating functions of the MRI apparatus according to the present embodiment.

FIG. 3 is a block diagram illustrating functions of the MRI apparatus 10 according to the present embodiment.

When the controller 37 (or the sequencer 30) executes a program, the MRI apparatus 10 functions as an operation support 61, an imaging region setting 62, a prior image generation 63, a patient information setting 64, a coefficient determination 65, an imaging condition setting 66, an SAR computing 67, and a main imaging execution 68 as illustrated in FIG. 3. Although the component members 61 through 68 of the MRI apparatus 10 are described to be operative as software, some or all of the component members 61 through 68 may be provided as circuitries in the MRI apparatus 10.

The operation support 61 is an interface such as a graphical user interface (GUI) configured as an interface among the component members 62 through 68, the display device 35, and the input device 36.

The imaging region setting 62 has a function of setting an imaging region (imaging position) with respect to the object P (illustrated in FIG. 1). For example, the imaging region setting 62 sets an imaging region (such as a whole body, a head, a chest, and an abdomen) based on an input signal input by the operator by using the input device 36 on the imaging condition edit screen. For example, the imaging region setting 62 also sets an imaging region by identifying a structure of volume data obtained when the later-described prior image generation 63 performs a volume scan. For example, the imaging region setting 62 further sets an imaging region based on a coil element for receiving an NMR signal, among the reception coils 28a to 28e, which is set based on an input signal input by the operator by using the input device 36, and also based on a direction (head first or feet first) to insert the object P (illustrated in FIG. 1) onto the mount.

The prior image generation 63 has a function of controlling operation of the imaging system 11 in the loaded condition in accordance with imaging conditions for prior imaging (imaging for setting parameters of the imaging condition for main imaging) performed before the main imaging so as to image the imaging region set by the imaging region setting 62 and to generate each original image which is a cross section image. Specifically, the prior image generation 63 generates as an original image one cross sectional image out of three orthogonal cross section images: an axial (AX) image; a sagittal (SG) image; and a coronal (CO) image.

The prior image generation 63 may reconstruct the AX image and the CO image, which are included in the three orthogonal cross section images, based on the SG image. The CO image and the AX image are each displayed on the display device 35 via the operation support 61.

The patient information setting 64 has a function of setting patient information on the imaging condition edit screen displayed via the operation support 61. The patient information (such as an ID, a height, a weight, and a body fat percentage) on the imaging condition edit screen is set based on examination order information transmitted from external devices (not illustrated), such as a hospital information system (HIS), via a network, or on an input from the input device 36.

The coefficient determination 65 has a function of determining a coefficient F ("F" included in Expressions (4) to (9)) to be multiplied by the RF power (high frequency pulse power absorbed by other than the object P) in the unloaded condition stored in the storage 34, in accordance with a volume of the object P (illustrated in FIG. 1). The volume of the object P can be computed based on at least one of a weight of the object P, a height of the object P, and an imaging region. The coefficient determination 65 can also determine the coefficient in accordance with the volume of the object P and a body fat percentage of the object P. In that case, accuracy of the SAR to be computed is further enhanced.

The imaging region representing the volume of the object P is set by the imaging region setting 62. The weight and height of the object P, and the body fat percentage of the object P, which represent the volume of the object P, are set by the patient information setting 64.

The coefficient determination 65 may acquire the coefficient corresponding to the volume of the object P from a correspondence table prepared in advance, the correspondence table including correspondence between a plurality of volumes and a plurality of coefficients.

Figure 4:
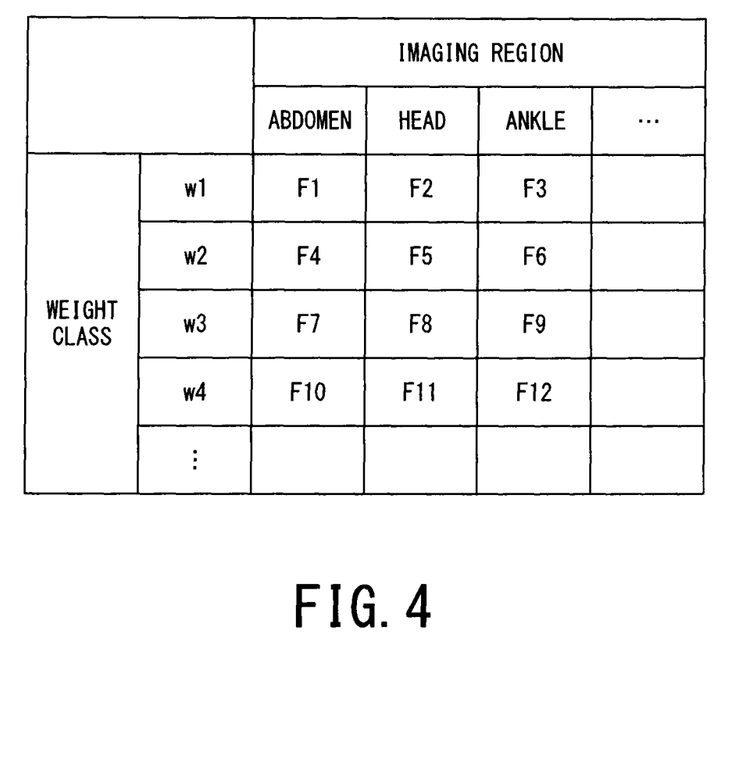
FIG. 4 is a diagram illustrating one example of a correspondence table of a coefficient prestored in a storage.

FIG. 4 is a diagram illustrating one example of the correspondence table of the coefficient F prestored in the storage 34.

FIG. 4 illustrates the correspondence table of the coefficients F each determined by a combination of a weight class to which a weight of the object P (illustrated in FIG. 1) belongs and an imaging region. When the object P has a weight belonging to a weight class w1, and the imaging region of the object P is "abdomen", the coefficient F is determined to be "F1." Similarly, when the object P has a weight belonging to the weight class w1, and the imaging region is "head", the coefficient F is determined to be "F2." In other combinations, the coefficient F is similarly determined to be "F3" to "F12" depending on the combination of the weight class and the imaging region.

Even in the cases of the same weight class and the same imaging region, different coefficient values are provided if intensities of a static magnetic field provided by the static magnetic field magnet 21 (illustrated in FIG. 1) are different. Therefore, it is preferable to provide a correspondence table for each static magnetic field intensity. Depending on each static magnetic field intensity, a correspondence table is acquired from the plurality of correspondence tables prepared in advance.

The correspondence table illustrated in FIG. 4 is obtained by simulation. The correspondence table illustrated in FIG. 4 includes twelve coefficients "F1" to "F12" corresponding to respective combinations of four weight classes and three imaging regions. However, the coefficients are not limited to these twelve coefficients.

With reference again to FIG. 3, the imaging condition setting 66 has a function of setting imaging conditions on the imaging condition edit screen displayed via the operation support 61. The imaging conditions including a pulse sequence, an imaging slice position, and positioning information of the table-top 24a (illustrated in FIG. 1) are set based on imaging conditions included in examination order information or on an input from the input device 36.

The SAR computing 67 has a function of computing an SAR by using a pulse energy method based on a value obtained by multiplying the RF power in the unloaded condition stored in the storage 34 by a coefficient determined by the coefficient determination 65. More specifically, the SAR computing 67 can determine the RF power in the unloaded condition in accordance with the volume of the object P, and can compute the SAR with the determined RF power.

The SAR computing 67 computes at least one of the whole body SAR with respect to the whole body of the object P, the body part SAR with respect to an imaging region, the head SAR with respect to the head, and the local SAR as the SAR. For example, when the imaging region set by the imaging region setting 62 is the whole body, the whole body SAR and the head SAR are computed. When the imaging region does not include the whole body nor the head, the body part SAR is computed. When the imaging region includes not the whole body but the head, the head SAR and the body part SAR are computed. When the imaging region is a subregion which does not include the head, the local SAR (an average value over bodily tissues of 10 [g]) is computed.

Specifically, the SAR computing 67 computes a whole body SAR ($SAR_{W'}$), a body part SAR ($SAR_{I'}$), and a head SAR ($SAR_{H'}$) by Expressions (4) to (6). The whole body $SAR_{W'}$ is computed by Expression (4) based on an RF power $P_W$ in the loaded condition, which is predicted based on an RF power obtained from the AD converter 46 (illustrated in FIG. 2) in the prior imaging performed by the prior image generation 63 and on the imaging conditions, an RF power $P_e$ in the unloaded condition stored in the storage 34, a coefficient F determined by the coefficient determination 65, and an entire weight $W_W$ of the object P. The body part $SAR_{I'}$ is computed by Expression (5) based on a body part $P_I$ of the RF power $P_W$ in the loaded condition, the RF power $P_e$ in the unloaded condition, the coefficient F and a partial weight $W_I$. The head $SAR_{H'}$ is computed by Expression (6) based on a head portion $P_H$ of the RF power $P_W$ in the loaded condition, the RF power $P_e$ in the unloaded condition, the coefficient F, and a head weight $W_H$.

$$SAR_{W'}[W/kg] = \frac{P_W[W] - P_e[W] \times F}{W_W[kg]} = \frac{P_W[W] - P_{e'}[W]}{W_W[kg]} \quad (4)$$

$$SAR_{I'}[W/kg] = \frac{P_I[W] - P_e[W] \times F}{W_I[kg]} = \frac{P_I[W] - P_{e'}[W]}{W_I[kg]} \quad (5)$$

$$SAR_{H'}[W/kg] = \frac{P_H[W] - P_e[W] \times F}{W_H[kg]} = \frac{P_H[W] - P_{e'}[W]}{W_H[kg]} \quad (6)$$

The partial weight $W_I$ in Expression (5) and the head weight $W_H$ in Expression (6) are estimated based on the volume (weight), the height, and the like of the object P. The body part $P_I$ in Expression (5) is obtained by multiplying an irradiation ratio [%] based on a correspondence table (not illustrated) illustrating a correspondence between the partial weight $W_I$ and the irradiation ratio [%] by the RF power $P_W$ in the loaded condition. The head portion $P_H$ in Expression (6) is obtained by multiplying an irradiation ratio [%] based on a correspondence table (not illustrated) illustrating a correspondence between the head weight $W_H$ and the irradiation ratio [%] by the RF power $P_W$ in the loaded condition.

As the RF power $P_e$ [W] used in the unloaded condition expressed in Expressions (1) to (3), a fixed value is used, whereas as the RF power $P_e'$ in the unloaded condition expressed in Expressions (4) to (5), a variable based on the coefficient F in the correspondence table illustrated in FIG. 4 is used.

Here, assume that the RF power $P_e$ in the unloaded condition stored in the storage 34 is a peak value of the RF power obtained from the AD converter 46 (illustrated in FIG. 2) when the MRI apparatus 10 is installed, and the RF power $P_W$ in the loaded condition is a peak value under the condition of 90 degrees. In this case, Expressions (4) to (6) are deformed into Expressions (7) to (9) with a duty cycle (irradiation time of RF pulse per unit time) D.

$$SAR_{W'} [W/kg] = \frac{(P_W[W] - P_e[W] \times F) \times \frac{D[\%]}{100}}{W_W[kg]} = \frac{(P_W[W] - P_{e'}[W]) \times \frac{D[\%]}{100}}{W_W[kg]} \quad (7)$$

$$SAR_{I'} [W/kg] = \frac{(P_I[W] - P_e[W] \times F) \times \frac{D[\%]}{100}}{W_I[kg]} = \frac{(P_I[W] - P_{e'}[W]) \times \frac{D[\%]}{100}}{W_I[kg]} \quad (8)$$

$$SAR_{H'} [W/kg] = \frac{(P_H[W] - P_e[W] \times F) \times \frac{D[\%]}{100}}{W_H[kg]} = \frac{(P_H[W] - P_{e'}[W]) \times \frac{D[\%]}{100}}{W_H[kg]} \quad (9)$$

As the RF power $P_e'$ in the unloaded condition expressed in Expressions (7) to (9), a variable is used as in the case of the RF power $P_e'$ in the unloaded condition expressed in Expressions (4) to (6).

The SAR computing 67 displays the SAR on the display device 35 via the operation support 61. The imaging condition setting 66 may change and reset the imaging conditions so that the SAR computed by the SAR computing 67 becomes equal to or below the upper limit (limit value) according to the IEC standards or other standards.

The main imaging execution unit 68 has an interlock function. When all the SARs computed by the SAR computing 67 are not more than (or below) their respective upper limits (limits), the main imaging execution unit 68 controls the operation of the imaging system 11 in accordance with the imaging conditions set by the imaging condition setting 66 so as to execute main imaging of an imaging region set by the imaging region setting 62 to provide images for diagnosis. The main imaging execution unit 68 also has a function of prohibiting the main imaging when any one of the SARs computed by the SAR computing 67 is above (or not less than) the upper limit.

Figure 5:
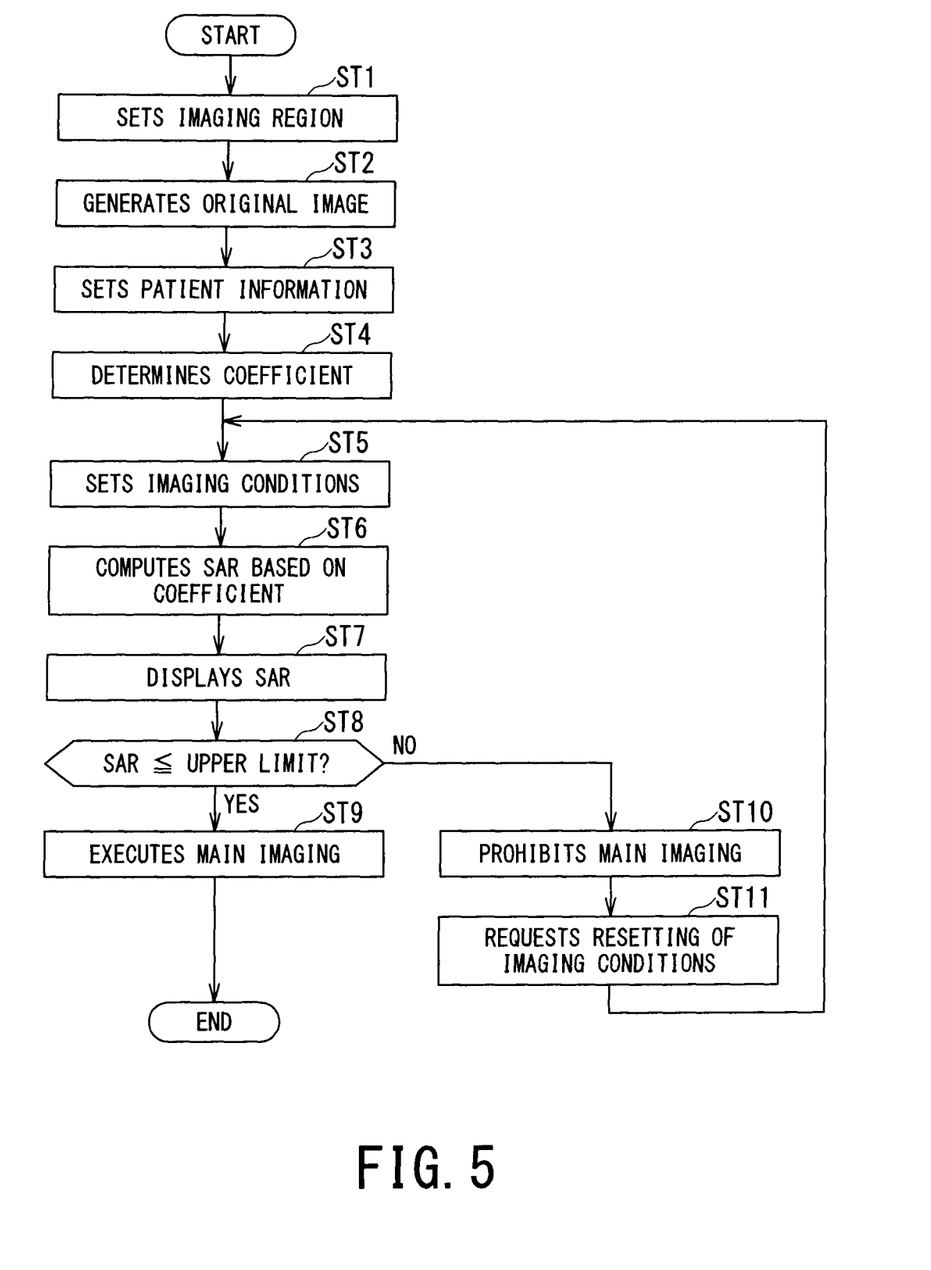
FIG. 5 is a flow chart illustrating an operation of the MRI apparatus according to the present embodiment.

A description is now given of the operation of the MRI apparatus 10 of this embodiment with reference to FIGS. 1 and 5.

FIG. 5 is a flow chart illustrating an operation of the MRI apparatus 10 according to the present embodiment.

The MRI apparatus 10 sets the imaging region of the object P (step ST1). The MRI apparatus 10 controls the operation of the imaging system 11 in the loaded condition in accordance with the imaging conditions for the prior imaging performed prior to the main imaging, so as to image the imaging region set in step ST1 and to generate an original image which is a cross sectional image (step ST2). The original image is displayed on the display device 35.

The MRI apparatus 10 sets patient information on the displayed imaging condition edit screen (step ST3). The MRI apparatus 10 determines the coefficient F in Expressions (4) to (9) in accordance with at least one parameter out of the imaging region set in step ST1, the weight of the object P, and the height of the object P included in the patient information set in step ST3 (step ST4).

The MRI apparatus 10 sets the imaging conditions for main imaging (step ST5). The imaging conditions are set based on the examination order information transmitted from external devices (not illustrated), such as an HIS, via the network, and on the input from the input device 36.

The MRI apparatus 10 computes the SAR by Expressions (4) to (9) based on an RF power $P_W$ in the loaded condition, which is predicted based on an RF power obtained from the AD converter 46 (illustrated in FIG. 2) in the prior imaging of step ST2 and on the imaging conditions set in step ST5, and an RF power $P_e'$ (variable) in the unloaded condition obtained by multiplying the RF power $P_e$ in the unloaded condition stored in the storage 34 by the coefficient F determined in step ST4 (step ST6). In step ST6, the MRI apparatus 10 computes at least one of the whole body SAR, the body part SAR, the head SAR, and the local SAR as an SAR. The MRI apparatus 10 displays the SAR computed in step ST6 on the display device 35 (step ST7).

The MRI apparatus 10 determines whether or not all the SARs computed in step ST6 are equal to or below the upper limit (step ST8). If YES in step ST8, that is, if it is determined that all the SARs are equal to or below the upper limit, the MRI apparatus 10 controls the operation of the imaging system 11 in accordance with the imaging conditions set in step ST5 to execute main imaging of the imaging region set by step ST1 to provide images for use in diagnosis (step ST9).

If No in step ST8, that is, if it is determined that any one of SARs is above the upper limit, the MRI apparatus 10 prohibits the main imaging (step ST10). The MRI apparatus 10 then requests resetting of the imaging conditions set in step ST5 (step ST11), and returns to step ST5.

According to the MRI apparatus 10 of the present embodiment, accurate and precise SARs can be computed by using the RF power $P_e'$ (variable) obtained by multiplying the RF power $P_e$ in the unloaded condition by the coefficient corresponding to the volume of the object. Using the accurate and precise SARs can solve the defect of deteriorated convenience due to the imaging being excessively limited and the defect of deteriorated safety due to the imaging being permitted beyond limits.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus, comprising:
a static magnetic field generator configured to generate a static magnetic field;
a gradient magnetic field generator configure to generate a gradient magnetic field;
a transmission coil configured to apply a radio frequency (RF) pulse to an object; and
processing circuitry configured to
correct an unloaded high frequency pulse power absorbed by other than the object with a volume of the object and a body fat percentage of the object to generate corrected high frequency pulse power,
determine a determined high frequency pulse power by subtracting the corrected high frequency pulse power from a loaded high frequency pulse power, and
compute a specific absorption rate (SAR) by dividing the determined high frequency pulse power by a weight of the object.

2. The magnetic resonance imaging apparatus according to claim 1, wherein the processing circuitry is further configured to determine the volume of the object based on at least one of a weight of the object, a height of the object, and an imaging region.

3. The magnetic resonance imaging apparatus according to claim 1, wherein the processing circuitry is further configured to compare the SAR with a limit value and to interlock main imaging.

4. A magnetic resonance imaging apparatus, comprising:
a static magnetic field generator configured to generate a static magnetic field;
a gradient magnetic field generator configured to generate a gradient magnetic field;
a transmission coil configured to apply a radio frequency (RF) pulse to an object;
processing circuitry configured to
determine a coefficient in accordance with a volume of the object, the coefficient being multiplied by an unloaded high frequency pulse power supplied to the transmission coil in an unloaded condition,
correct the unloaded high frequency pulse power absorbed by other than the object by multiplying the unloaded high frequency pulse power by the coefficient to generate corrected high frequency pulse power,
determine a determined high frequency pulse power by subtracting the corrected high frequency pulse power from a loaded high frequency pulse power, and
compute a specific absorption rate (SAR) by dividing the determined high frequency pulse power by a weight of the object.

5. The magnetic resonance imaging apparatus according to claim 4, wherein the processing circuitry is further configured to determine the coefficient based on at least one of a weight of the object, a height of the object, and an imaging region.

6. The magnetic resonance imaging apparatus according to claim 4, wherein the processing circuitry is further configured to compare the SAR with a limit value and to interlock main imaging.

7. The magnetic resonance imaging apparatus according to claim 4, wherein the processing circuitry is further configured to determine the coefficient in accordance with the volume of the object and a body fat percentage of the object.

8. The magnetic resonance imaging apparatus according to claim 4, wherein the processing circuitry is further configured to acquire the coefficient corresponding to the volume of the object from a correspondence table prepared in advance, the correspondence table including correspondence between a plurality of volumes and a plurality of coefficients.

9. The magnetic resonance imaging apparatus according to claim 8, wherein the processing circuitry is further configured to acquire, out of the plurality of correspondence tables prepared in advance, a correspondence table corresponding to an intensity of the static magnetic field generated by the static magnetic field generator.

10. A specific absorption rate (SAR) computing method in a magnetic resonance imaging apparatus including a static magnetic field generator, a gradient magnetic field generator and a transmission coil configured to apply a radio frequency (RF) pulse to an object, the method comprising:
correcting an unloaded RF pulse power absorbed by other than the object with a volume of the object and a body fat percentage of the object to generate corrected RF pulse power;
determining a determined high frequency pulse power by subtracting the corrected RF pulse power from a loaded high frequency pulse power; and
computing an SAR by dividing the determined high frequency pulse power by a weight of the object.

11. A specific absorption rate (SAR) computing method in a magnetic resonance imaging apparatus including a static magnetic field generator, a gradient magnetic field generator a nd a transmission coil configured to apply a radio frequency (RF) pulse to an object, the method comprising:
determining a coefficient in accordance with a volume of the object, the coefficient being multiplied by an unloaded high frequency pulse power supplied to the transmission coil in an unloaded condition;
correcting the unloaded high frequency pulse power absorbed by other than the object by multiplying the unloaded high frequency pulse power by the coefficient to generate corrected high frequency pulse power;
determining a determined high frequency pulse power by subtracting the corrected high frequency pulse power from a scheduled loaded high frequency pulse power; and
computing an SAR by dividing the determined high frequency pulse power by a weight of the object.

* * * * *